(12) United States Patent
Baron et al.

(10) Patent No.: US 8,785,491 B2
(45) Date of Patent: Jul. 22, 2014

(54) PHARMACEUTICAL COMPOSITIONS AND METHODS FOR TREATING AGE-RELATED MACULAR DEGENERATION WITH MELATONIN ANALOGUES

(75) Inventors: David Baron, Skokie, IL (US); Keisuke Hirai, Osaka (JP); Yasushi Shintani, Osaka (JP); Osamu Uchikawa, Osaka (JP)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 0 days.

(21) Appl. No.: 13/063,672

(22) PCT Filed: Jun. 17, 2009

(86) PCT No.: PCT/US2009/047669
§ 371 (c)(1),
(2), (4) Date: Jun. 9, 2011

(87) PCT Pub. No.: WO2010/008746
PCT Pub. Date: Jan. 21, 2010

(65) Prior Publication Data
US 2011/0229464 A1    Sep. 22, 2011

Related U.S. Application Data

(60) Provisional application No. 61/073,963, filed on Jun. 19, 2008.

(51) Int. Cl.
*A01N 43/08* (2006.01)
*A61K 31/34* (2006.01)
(52) U.S. Cl.
USPC .......................................................... 514/468

(58) Field of Classification Search
CPC ... A61K 31/343; C07D 307/77; C07D 493/14
See application file for complete search history.

(56) References Cited

U.S. PATENT DOCUMENTS

| 6,034,239 | A  | * | 3/2000  | Ohkawa et al. ............... 544/147 |
| 6,663,883 | B1 |   | 12/2003 | Akiyama et al. |
| 6,800,086 | B2 |   | 10/2004 | Strong |
| 2003/0093065 | A1 | * | 5/2003 | Peyman ........................... 606/4 |
| 2005/0031651 | A1 |  | 2/2005 | Gervais et al. |
| 2007/0129441 | A1 |  | 6/2007 | Koulen |
| 2007/0197442 | A1 |  | 8/2007 | Pressler et al. |
| 2008/0132490 | A1 |  | 6/2008 | Bergman et al. |

FOREIGN PATENT DOCUMENTS

WO    2010/008746    1/2010

OTHER PUBLICATIONS

Yi et al. "Effects of Melatonin in Age-Related Macular Degeneration". Ann. N.Y. Acad. Sci. 1057: 384-392 (2005).*
Costa et al. "Intravitreal Bevacizumab for Choroidal Neovascularization Caused by AMD (IBeNa Study): Results of a Phase 1 Dose-Escalation Study". Invest Ophthalmol Vis Sci. 2006; 47:4569-4578.*
Xin, H. et al., "A novel organotype culture model of the postnatal mouse retina allows the study of glutamate-mediated excitotoxicity," J. Neurosci. Meth. (2007) 159:35-42.
International Search Report for Application No. PCT/US09/47669 dated Dec. 23, 2009 (2 pages).
Written Opinion for Application No. PCT/US09/47669 dated Dec. 23, 2009 (5 pages).

* cited by examiner

*Primary Examiner* — Leslie A. Royds Draper
(74) *Attorney, Agent, or Firm* — Michael Best & Friedrich LLP; Lisa V. Mueller

(57) ABSTRACT

Pharmaceutical compositions and methods for treating and/or preventing age-related macular degeneration with melatonin analogues are provided.

23 Claims, 2 Drawing Sheets

PHARMACEUTICAL COMPOSITIONS AND METHODS FOR TREATING AGE-RELATED MACULAR DEGENERATION WITH MELATONIN ANALOGUES

CROSS-REFERENCE TO RELATED APPLICATIONS

This is the U.S. national stage entry of International Patent Application No. PCT/US2009/047669, filed on Jun. 17, 2009, which claims priority to U.S. Provisional Patent Application No. 61/073,963, filed Jun. 19, 2008, the contents of all of which are hereby incorporated by reference.

STATEMENT REGARDING FEDERALLY SPONSORED RESEARCH

Not Applicable

THE NAMES OF THE PARTIES TO A JOINT RESEARCH AGREEMENT

Takeda Pharmaceutical Company, Ltd., a Japanese corporation, and Takeda Global Research and Development Co., Inc., a U.S. corporation, are parties to a joint research agreement.

REFERENCE TO ANY "SEQUENCE LISTING" APPENDIX

Not Applicable

BACKGROUND OF THE INVENTION

Age-related macular degeneration ("AMD") is defined by the gradual destruction of sharp, central vision in older individuals. The macular area of the retina processes central vision, and is adjacent to the optic nerve and near the center of the optic axis. AMD occurs in two forms, dry and wet.

Dry AMD is defined by the gradual loss of retinal pigment epithelial (RPE) and photoreceptor cells in the macula. Drusen, or yellow deposits under the retina, are often found in people over 60 and represent an early indication of developing AMD, but do not in and of themselves cause vision loss. Early AMD is defined by several small drusen or less frequent medium-sized drusen. Intermediate AMD is defined by more medium-sized drusen or a few large drusen. At this stage, visual disturbances may be reported. Advanced dry AMD is defined by loss of photoreceptors and supporting cell types in the macula with accompanying progressive vision loss.

Wet AMD is less common and is characterized by growth of abnormal blood vessels beneath the macular epithelium. These vessels are fragile and leak blood and exudates that separate the macular retina from underlying structures. Wet AMD advances more quickly than dry AMD. Rather than blurry vision characteristic of dry AMD, wet AMD is associated with the perception of straight-line grids as wavy especially at their center. The wet form develops in people who initially present with the dry form and is always considered an advanced form of AMD.

Current treatment for dry AMD consists of a regimen of specific high-dose anti-oxidants (vitamins C, E, beta carotene), and copper and zinc (National Eye Institute's Age-Related Eye Disease Study [AREDS] formulation) that reduce the risk of progression of intermediate AMD to advanced AMD. However, this treatment is not indicated for early AMD due to lack of efficacy. Wet AMD is treated with laser surgery to destroy abnormal vasculature but may not be indicated for most cases. New abnormal vessels may develop after initial treatment.

Photodynamic therapy is also used to destroy abnormal vessels.

Yet another treatment option is direct injection of the anti-VEGF (vascular endothelial growth factor) antibody fragment ranibizumab (LUCENTIS, Genentech) which is now approved for the treatment of wet AMD. This treatment may slow vision loss and in some cases actually improves vision. However, it requires intravitreal injection and subsequent monitoring for increases in ocular pressure. Retinal detachment or infection may occur along with red eye, vitreous floaters and pain. In addition, bevacizumab is currently being used off-label as an intravitreal injection to treat AMD (Costa et al., *Investigative Ophthamology and Visual Science*, 47: 4569-4578, 2006).

Melatonin has been shown to control eye pigmentation (i.e., melanin) and thereby regulate the amount of light that can reach the photoreceptors. Melatonin levels produced by the pineal gland are known to decrease with age in humans, as do levels of melanin in retinal pigment epithelial cells (RPE) (Sarna, T. et al., *Exp. Eye Res.*, 76: 89-98, 2003). Melatonin is also synthesized by photoreceptor cells with a circadian rhythm similar to that of the pineal gland (Weichmann, A. F., *Exp. Eye Res.*, 42: 507-527, 1986). The diminution may decrease the protection from oxidative damage afforded to the RPE by melanin. RPE dysfunction, which is thought to follow oxidative damage, is a well-known initiator of age-related macular degeneration (AMD).

Melatonin has been shown to protect human retinal pigment epithelial (RPE) cells in vitro when added diurnally to RPE cell cultures for three consecutive days. This treatment regimen markedly reduced $H_2O_2$-induced cell death and mitochondrial DNA damage (Liang, F.-Q., et al., *Exp. Eye Res.*, 78: 1069-1075, 2004). Other studies have shown that melanin itself protects the human RPE from light-induced apoptosis (Seagle, B.-L. L., et al., *Proc. Natl. Acad. Sci. U.S.A.*, 102: 8978-8983, 2005) and that melanin free radicals can quench reactive oxygen species (Seagle, B.-L. L., et al. *J. Am. Chem. Soc.*, 127: 11220-11221, 2005). These studies are of interest because melatonin, and presumably its analogs, can raise the level of melanin in the RPE.

A case-controlled study of dry and wet AMD has recently shown that 3 mg melatonin administered daily at bedtime for at least three months may reduce the extent of retinal pathology over time. Visual acuity remained stable, and the change in the picture of the fundus was remarkable in that few of the examined eyes showed either more retinal bleeding or exudates (Yi, C. et al., *Ann. N.Y. Acad. Sci.*, 1057: 384-392, 2005).

Melatonin is available over the counter in the US generally as a 3 mg tablet for relief from insomnia or jetlag, but has never been fully tested for efficacy or safety and therefore is sold as an over the counter dietary supplement.

Ramelteon is a melatonin analog described in U.S. Pat. No. 6,034,239 (hereby incorporated by reference in the entirety), and is currently FDA approved for marketing in the US for treatment of sleep disorders. This non-addictive compound is available in an 8 mg tablet, and numerous GCP compliant clinical trials and drug-drug interaction studies have shown that ramelteon is safe for humans at significant multiples of the therapeutic dose. Ramelteon, a sleep-promoting agent, is chemically designated as (S)—N-[2-(1,6,7,8-tetrahydro-2H-indeno-[5,4-b]furan-8-yl)ethyl]propionamide, and is a selective melatonin receptor agonist with high affinity for melatonin $MT_1/MT_2$ receptors. As a sleep aid, ramelteon appears to act more as a "switch" rather than exhibiting prominent dose-dependent pharmacology.

Melatonin, melatonin analogues and anti-VEGF agents have all been proposed as useful pharmacological agents for the treatment of glaucoma. Specifically, it has been suggested that melatonin may be useful for the treatment of glaucoma (Lundmark et al., *Exp. Eye Res.*, 84: 1021-1030, 2007; U.S. Pat. No. 4,654,361 and U.S. Patent Application Publication No. 2007/0207116); U.S. Pat. No. 6,034,239 indicates that ramelteon is useful to treat various disorders accompanies by aging, and also that ramelteon may be useful to treat glaucoma; and off-label use of either bevacizumab or ranibuzumab to treat glaucoma with positive results has been reported (Ichhpujani et al., *Can. J. Ophthamol.*, 42: 812-815, 2007; Cheng et al., *Annals Academy of Medicine*, 37: 72-74, 2008; Dunavoelgyi et al., *Clinical and Experimental Ophthamology*, 35:878-880, 2007).

BRIEF SUMMARY OF THE INVENTION

The present invention teaches pharmaceutical compositions and methods for the treatment of age-related macular degeneration in a patient in need thereof. In particular, the present invention teaches the administration of ramelteon or its metabolite, for the treatment and/or prevention of AMD in a patient in need thereof. More specifically, patients identified as having AMD or at high risk for developing AMD can be treated with therapeutic and/or prophylactic amounts of "ramelteon and/or its metabolite" for preventing or inhibiting the progression of disease.

Thus the present invention teaches specific formulations of ramelteon and/or its metabolite pharmaceutical compositions suitable for administration to a patient in need of treatment for AMD, for the prophylactic treatment against AMD, or for the therapeutic and/or prophylactic prevention of advancement of AMD disease in a patient in need thereof.

The present invention teaches a method for treating and/or preventing age-related macular degeneration in a patient identified as in need thereof, said method comprising identifying a patient in need of treatment for age-related macular degeneration, and administering a therapeutic amount of ramelteon to said patient.

The present invention teaches a method as above, wherein the patient is identified via visual examination of the patient's eye.

The present invention teaches a method as above, wherein the patient is identified via screening according to risk-factor criteria.

The present invention teaches a method as above, wherein said age-related macular degeneration is the dry form.

The present invention teaches a method as above, wherein said age-related macular degeneration is the wet form.

The present invention teaches a method as above, wherein said age-related macular degeneration occurs in one eye.

The present invention teaches a method as above, wherein said age-related macular degeneration occurs in two eyes.

The present invention teaches a method as above, wherein said administration of ramelteon is via an oral dosage form.

The present invention teaches a method as above, wherein said administration of ramelteon is via an injectible dosage form.

The present invention further teaches a method wherein said administration of ramelteon is via a surface absorbent dosage form.

The present invention teaches wherein said administration of ramelteon is via a skin-patch dosage form.

The present invention teaches wherein said administration of ramelteon is via a liquid, powder, ointment, paste, gel or cream dosage form.

The present invention teaches wherein said ramelteon is administered in a dose of from 1 mg to 1000 mg.

The present invention teaches a method wherein said ramelteon is administered as an isolated metabolite of ramelteon, (S)—N-[2-[4-hydroxy-1,6,7,8-tetrahydro-2H-indeno[5,4-b]furan-8-yl]ethyl]propionamide (hereinafter, sometimes referred to as metabolite 1), in a dose of from 1 mg to 1000 mg.

The present invention teaches wherein administration of a therapeutic amount of ramelteon results in a serum concentration of metabolite 1 of from 1 µg/L to 100 mg/L.

The present invention teaches wherein said ramelteon is administered in a dose once daily.

The present invention teaches wherein said ramelteon is administered in the evening.

The present invention teaches wherein said ramelteon is administered prior to sleep.

The present invention also teaches wherein said ramelteon is administered in a dose twice daily.

The present invention teaches wherein said ramelteon is administered in a dose more than twice daily.

The present invention teaches wherein administration of a therapeutic amount of ramelteon results in a serum concentration of metabolite 1 of from 1 µg/L to 100 mg/L.

The present invention teaches wherein administration of a therapeutic amount of ramelteon results in a serum concentration of metabolite 1 of from 1 µg/L to 100 mg/L.

The present invention further teaches a pharmaceutical composition comprising a therapeutic amount of ramelteon, and/or a therapeutic amount of an isolated metabolite of ramelteon, metabolite 1, and a pharmaceutically acceptable carrier, excipient or diluent.

DETAILED DESCRIPTION OF THE INVENTION

Figure 1:
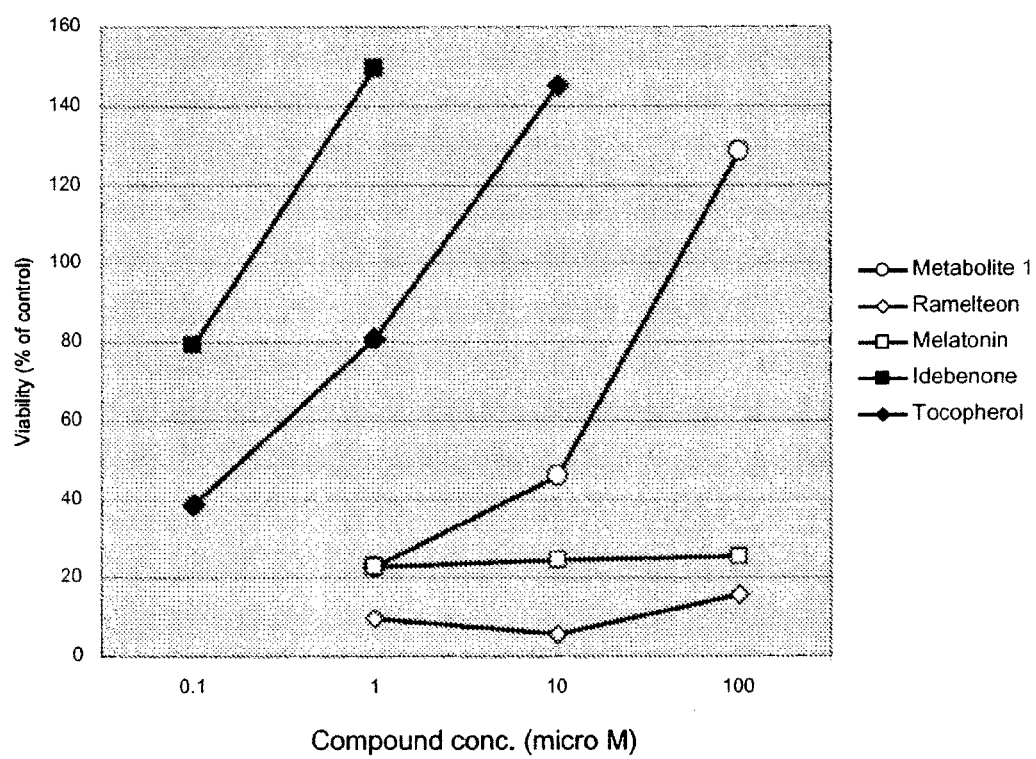
FIG. 1 is a graph of the amount of cell viability retained after treating a glutamate-containing cell culture medium with ramelteon and metabolite 1 against idebenone, tocopherol and melatonin as described in Example 2.

As described above, "ramelteon" is a known compound which is described in U.S. Pat. No. 6,034,239, and which has the following chemical name: (S)—N-[2-(1,6,7,8-tetrahydro-2H-indeno[5,4-b]furan-8-yl)ethyl]propionamide.

As described above, the term "metabolite 1" as used in the present specification means the metabolite of ramelteon which has the following chemical name: (S)—N-(2-[4-hydroxy-1,6,7,8-tetrahydro-2H-indeno[5,4-b]furan-8-yl]ethyl)propionamide.

Ramelteon and metabolite 1 can be prepared according to or analogously to a method described in the above-mentioned U.S. patent. The compounds are melatonin receptor agonists.

Age-related macular degeneration (AMD) means the pathological condition of the retina which is characterized by physical changes in the macular region of the retina and presents with loss of central vision in the patient.

AMD can be diagnosed by physical direct or indirect examination of the retina to detect and/or identify characteristic physical appearances of the macular region of the retina which are not considered normal. In particular, the identification of drusen deposits in the case of dry AMD, or abnormal blood vessel formations in the case of wet AMD. Patients with a propensity for AMD, or an increased risk for AMD can be identified via selection criteria scored according to risk factors. The selection criteria include physical factors such as age of patient (the older, the greater the risk); family history (if yes, then greater risk), and occupational or environmental factors such as exposure to bright sunlight (the greater the exposure, the greater the risk); exposure to bright lights (the greater the exposure, the greater the risk).

Ramelteon acts as a melatonin agonists in mammals (e.g., mouse, rat, hamster, rabbit, feline, canine, bovine, sheep, monkey, human, etc.) and is useful as a composition with a binding affinity for melatonin receptor, especially a composition agonistic towards melatonin receptors. Metabolite 1 also has a binding affinity for the melatonin receptor in mammals (e.g., mouse rat, hamster, rabbit, feline, canine, bovine, sheep, monkey, human, etc).

Ramelteon and metabolite 1 can be used for preventing and treating AMD.

Ramelteon has low toxicity and can be administered safely through per oral or parenteral routes (e.g., for local administration, rectal administration, intravenous administration, etc.), either directly or as pharmaceutical compositions to be mixed with pharmaceutically acceptable carriers by using known methods, for example, as tablets (including sugar-coated tablets, film-coated tablets), powders, granules, capsules (including soft capsules), liquids, eye drops, injections, suppositories, sustained release preparations, plasters and also as chewing gum, etc. Administration may be oral, by inhalation, topical, transmucosal, parenteral, intravenous or intraocular.

Pharmacologically acceptable carriers that may be used to produce the pharmaceutical compositions of the present invention include various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonizing agents, buffers and soothing agents for liquid preparations. Other ordinary pharmaceutical additives such as preservatives, antioxidants, coloring agents, sweetening agents, souring agents, bubbling agents and flavorings may also be used as necessary.

Such "excipients" include, for example, lactose, sucrose, D-mannitol, starch, cornstarch, crystalline cellulose, light silicic anhydride and titanium oxide.

Such "lubricants" include, for example, magnesium stearate, sucrose fatty acid esters, polyethylene glycol, talc and stearic acid.

Such "binders" include, for example, hydroxypropyl cellulose, hydroxypropylmethyl cellulose, crystalline cellulose, polyvinylpyrrolidone, gum arabic powder, gelatin, pullulan and low-substitutional hydroxypropyl cellulose.

Such "disintegrants" include (1) crosslinked povidone, (2) super-disintegrants such as crosslinked carmellose sodium (FMC-Asahi Chemical) and carmellose calcium (Gotoku Yakuhin), (3) carboxymethyl starch sodium (e.g., product of Matsutani Chemical), (4) low-substituted hydroxypropyl cellulose (e.g., product of Shin-Etsu Chemical), (5) cornstarch, and so forth. Said "crosslinked povidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP) and Polyplasdon INF-10 (produced by ISP).

Such "water-soluble polymers" include, for example, ethanol-soluble water-soluble polymers [e.g. cellulose derivatives such as hydroxypropyl cellulose (hereinafter also referred to as HPC), polyvinylpyrrolidone] and ethanol-insoluble water-soluble polymers [e.g., cellulose derivatives such as hydroxypropylmethyl cellulose (hereinafter also referred to as HPMC), methyl cellulose and carboxymethyl cellulose sodium, sodium polyacrylate, polyvinyl alcohol, sodium alginate, guar gum].

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate, etc. Such basic inorganic salts of potassium include, for example, potassium carbonate, potassium hydrogen carbonate, etc. Such basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite $[Mg_6Al_2(OH)_{16}CO_3.4H_2O]$ and so forth. Among others, preferred is heavy magnesium carbonate, magnesium carbonate, magnesium oxide, magnesium hydroxide, etc. Such basic inorganic salts of calcium include, for example, precipitated calcium carbonate, calcium hydroxide, etc.

Such "solvents" include, for example, water for injection, alcohol, propylene glycol, macrogol, sesame oil, corn oil and olive oil.

Such "dissolution aids" include, for example, polyethylene glycol, propylene glycol, D-mannitol, benzyl benzoate, ethanol, trisaminomethane, cholesterol, triethanolamine, sodium carbonate and sodium citrate.

Such "suspending agents" include, for example, surfactants such as stearyltriethanolamine, sodium lauryl sulfate, laurylaminopropionic acid, lecithin, henzalkonium chloride, henzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Such "isotonizing agents" include, for example, glucose, D-sorbitol, sodium chloride, glycerol and D-mannitol.

Such "buffers" include, for example, buffer solutions of phosphates, acetates, carbonates, citrates etc.

Such "soothing agents" include, for example, benzyl alcohol.

Such "preservatives" include, for example, p-oxybenzoic acid esters, chlorobutanol, benzyl alcohol, phenethyl alcohol, dehydroacetic acid and sorbic acid.

Such "antioxidants" include, for example, sulfites, ascorbic acid and alpha D-tocopherol.

Such "coloring agents" include, for example, food colors such as Food Color Yellow No. 5, Food Color Red No. 2 and Food Color Blue No. 2; and food lake colors and red oxide.

Such "sweetening agents" include, for example, saccharin sodium, dipotassium glycyrrhetinate, aspartame, stevia and thaumatin.

Such "souring agents" include, for example, citric acid (citric anhydride), tartaric acid and malic acid.

Such "bubbling agents" include, for example, sodium bicarbonate.

Such "flavorings" may be synthetic substances or naturally occurring substances, and include, for example, lemon, lime, orange, menthol and strawberry.

The content of ramelteon or metabolite 1 is usually about 0.01 to 100% by weight based on a total weight of the composition.

Specifically, the composition comprising ramelteon or metabolite 1 can be prepared according to or analogously to the method described in U.S. Pat. No. 6,034,239.

Furthermore, ramelteon or metabolite 1 can also be used in combination with other drugs such as H1 antagonists, anti-VEGF antibodies, anti-VEGF aptamer, VEGF receptor protein kinase inhibitor, synthetic steroid, vitamin A, vitamin C, vitamin E, β carotene, lutein and zinc. An example of an aptamer is pegaptanib sodium. Examples of antibodies include bevacizumab and ranibizumab.

The composition comprises the other drugs are prepared by using known methods, for example, as tablets (including sugar-coated tablets, film-coated tablets), powders, granules, capsules (including soft capsules), liquids, injections, suppositories, sustained release preparations, plasters and also as chewing gum, etc. The compound may be administered as an immediate release form, a controlled release form or a sustained release form.

When ramelteon or metabolite 1 is used in combination with the other drugs, examples of administration forms include (1) administration of a single preparation obtained by formulating ramelteon or metabolite 1 and the other drugs simultaneously, (2) simultaneous administration of two preparations obtained by formulating ramelteon or metabolite 1 and the other drugs separately, via an identical route, (3) sequential and intermittent administration of two preparations obtained by formulating ramelteon or metabolite 1 and the other drugs separately, via an identical route, (4) simultaneous administration of two preparations obtained by formulating ramelteon or metabolite 1 and the other drugs separately, via different routes, (5) sequential and intermittent administration of two preparations obtained by formulating ramelteon or metabolite 1 and the other drugs separately, via different routes (e.g. administration in the order of ramelteon or metabolite 1 then the other drugs, or in the inverse order) and the like. From a viewpoint of convenience of patients, preferred is an administration of a single preparation obtained by formulating ramelteon or metabolite 1 and the other drugs simultaneously.

The dose of ramelteon or metabolite 1 differs depending on an administration subject, and administration route. For example, as a therapeutic agent for AMD, the dosage is about 0.0005 to 2 mg/kg body weight, preferably about 0.001 to 1 mg/kg body weight, more preferably about 0.001 to 0.5 mg/kg body weight in terms of ramelteon or metabolite 1 as active ingredient for an adult. Especially, administration of a therapeutic amount of ramelteon results in a serum concentration of metabolite 1 of from 1 μg/L to 100 mg/L, preferably from 100 μg/L to 30 mg/L. The pharmaceutical composition may be administered once to several times in divided doses per day.

The dosage of the other drugs can be appropriately selected based on a clinically used dose. In addition, the blending ratio of melatonin receptor agonist and the other drugs can be appropriately selected depending on administration subject, administration route, target disease, symptom, the other drugs to be used and the like. Usually, the ratio may be decided based on the general dose of the other drugs to be used. When the administration subject is human, for example, 0.01-100 parts by weight of other drugs is used relative to 1 part by weight of ramelteon or metabolite 1.

The present invention will be described in detail through the following examples. The examples are intended to illustrate the present invention, but not to limit the scope of the present invention.

Reference Example 1

(S)—N-(2-[4-bromo-1,6,7,8-tetrahydro-2H-indeno[5,4-b]furan-8-yl]ethyl)propionamide

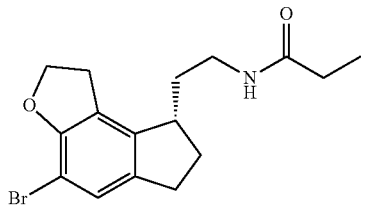 [SMILES: CCC(=O)NCC[C@@H]1CCc2cc(Br)c3c(c21)CCO3]

Bromine was added dropwise into a solution of (S)—N-(2-[1,6,7,8-tetrahydro-2H-indeno[5,4-b]furan-8-yl]ethyl)propionamide (27.4 g, 0.11 mol) and sodium acetate (10.4 g, 0.13 mol) in methanol (200 mL) with ice-cooling. The mixture was allowed to stir for 1.5 hours with ice-cooling, which was quenched with sodium hydrogen sulfite and poured into water, followed by extracting with ethyl acetate. The extracted solution was washed with water and a saturated aqueous solution of sodium hydrogencarbonate, which was dried over anhydrous magnesium sulfate, followed by distilling off the solvent under reduced pressure. The residue was purified by means of silica gel column chromatography (ethyl acetate:hexane=8:2) to afford the title compound (yield 33.1 g, 93%) as a white powder.

m.p.: 129-131° C. (recrystallized from ethyl acetate/hexane)

NMR (CDCl$_3$) δ: 1.15 (3H, t, J=7.5 Hz), 1.50-2.39 (4H, m), 2.19 (2H, q, J=7.5 Hz), 2.67-2.98 (2H, m), 3.02-3.42 (5H, m), 4.53-4.78 (2H, m), 5.47 (1H, br s), 7.11 (1H, s).

Elemental Analysis for $C_{16}H_{20}BrNO_2$:
Calcd.: C, 56.82; H, 5.96; N, 4.14; Br, 23.62.
Found: C, 56.84; H, 5.99; N, 4.14; Br, 23.66.

Reference Example 2

(S)—N-(2-[4-methoxy-1,6,7,8-tetrahydro-2H-indeno[5,4-b]furan-8-yl]ethyl)propionamide

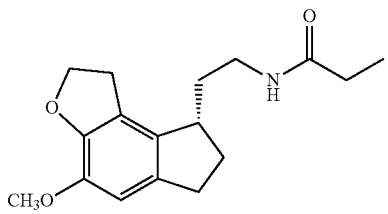

A solution of sodium methoxide (200 mL, 28% solution in methanol) was added dropwise into a mixture of (S)—N-(2-[4-bromo-1,6,7,8-tetrahydro-2H-indeno[5,4-b]furan-8-yl]ethyl)propionamide (5.00 g, 14.8 mmol), copper(I) bromide (2.12 g, 14.8 mmol) and methyl acetate (3.29 g, 44.3 mmol). The mixture was refluxed for 5 hours. The mixture was cooled, which was quenched with 1N HCl, followed by extracting with methanol-chloroform. The extracted solution was dried over anhydrous magnesium sulfate, followed by distilling off the solvent under reduced pressure. The residue was purified by means of silica gel column chromatography and recrystallized from ethyl acetate to afford the title compound (yield 2.58 g, 60%) as a white powder.

NMR (CDCl$_3$) δ: 1.14 (3H, t, J=7.5 Hz), 1.50-3.40 (13H, m), 3.84 (3H, s), 4.50-4.75 (2H, m), 5.43 (1H, br s), 6.63 (1H, s).

Elemental Analysis for $C_{17}H_{23}NO_3$:
Calcd.: C, 70.56; H, 8.01; N, 4.84.
Found: C, 70.66; H, 8.02; N, 5.04.

Example 1

(S)—N-(2-[4-hydroxy-1,6,7,8-tetrahydro-2H-indeno[5,4-b]furan-8-yl]ethyl)propionamide

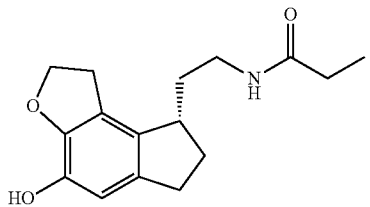 [SMILES: CCC(=O)NCC[C@@H]1CCc2cc(O)c3c(c21)CCO3]

Boron tribromide (6.92 mmol) was added dropwise into a solution of (S)—N-(2-[4-methoxy-1,6,7,8-tetrahydro-2H-indeno[5,4-b]furan-8-yl]ethyl)propionamide (1.00 g. 3.46 mmol) in methylene chloride (15 mL) at about −50° C. The mixture was stirred for 2 hours at temperatures ranging from −50 to 0° C. Crushed ice was added and the mixture was stirred for further 2 hours at room temperature, followed by extracting with methanol-chloroform. The extracted solution was dried over anhydrous magnesium sulfate, followed by distilling off the solvent under reduced pressure. The residue was purified by means of silica gel column chromatography (ethyl acetate) to afford the title compound (yield 320 mg, 34%) as a white powder. This compound is also referred to as metabolite 1.

m.p.: 149-152° C. (recrystallized from ethyl acetate/hexane)

NMR (CDCl$_3$) δ: 1.14 (3H, t, J=7.7 Hz), 1.52-2.33 (6H, m), 2.65-2.90 (1H, m), 3.05-3.40 (5H, m), 4.50-4.70 (2H, m), 5.11 (1H, s), 5.44 (1H, br s), 6.61 (1H, s).

Elemental Analysis for $C_{16}H_{21}NO_3$:
Calcd.: C, 69.79; H, 7.69; N, 5.09.
Found: C, 69.68; H, 7.67; N, 5.16.

Example 2

Effect Against Glutamate-Induced Cytotoxicity

We used ramelteon and metabolite 1 (as synthesized in Example 1) in this study. Idebenone and vitamine E (α-tocopherol) were purchased from Wako Pure Chemical Industries (Osaka, Japan) and used as positive control. All other chemicals were purchased from standard sources.

N18-RE-105 hybrid cells (mouse neuroblastoma clone N18TG-2 X Fisher rat 18-day embryonic neural retina) were cultured with Dulbecco's Modified Eagles Media (DMEM) supplemented with 5% fetal calf serum (FCS), and hypoxanthine, aminopterin, and thymidine at a 37° C. incubator with 5% $CO_2$. For cytotoxicity studies, cells were plated in 96-well plates at a density of 5,000 cells per well in 0.1 ml of the above medium. After culturing for 24 hr, the medium was removed and replaced with medium containing 10 mM glutamate with or without various concentrations of compounds. After 24 hours of incubation, cytotoxicity was quantitated by the release of the cytosolic enzyme lactate dehydrogenase (LDH) into the culture medium. The percentage of cell viability in the presence of each of the test compounds was calculated from the following formula: % cell viability in the presence of compound={LDH activity (absorbance at 550 nm) in the culture medium with compound plus 10 mM glutamate−LDH activity in the control culture medium/LDH activity in the culture medium with 10 mM glutamate−LDH activity in the control culture medium}×100.

Figure 2:
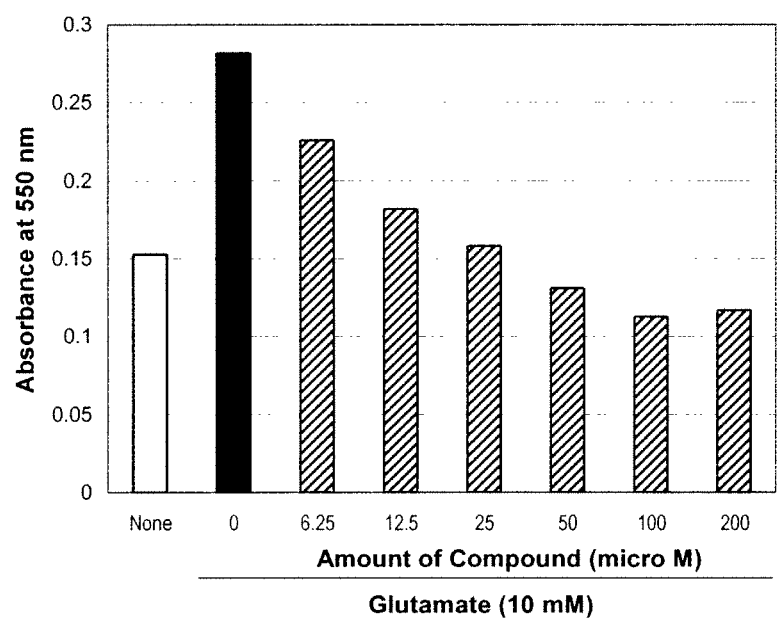
FIG. 2 is a graph of absorbance when a glutamate-containing cell culture is treated with varying concentrations of metabolite 1 as described in Example 2.

FIG. 1 shows the effects of compounds on cytotoxicity induced by 10 mM glutamate. Although the cytotoxicity by glutamate was inhibited by the treatment of metabolite 1, the incubation with melatonin or ramelteon did not affect cell viability. Higher concentrations of metabolite 1 significantly protected against glutamate cytotoxicity compared with the glutamate control. Notably the highest concentration of metabolite 1 completely prevented the toxicity of glutamate over the basal viability (FIGS. 1 and 2). Idebenone and tocopherol were used as positive controls to demonstrate that cell viability was increased with addition of these compounds in the presence of glutamate. Since cell death is implicated in age related macular degeneration, the fact that metabolite 1 increases cell viability indicates that metabolite 1 will be useful to counter the effects of age related macular degeneration.

FIG. 2 shows the amount of absorbance when the glutamate-containing cell cultures are treated with varying amounts of metabolite 1. The level of absorbance in the presence of no additives is indicated by the white bar. The solid bar shows the level of absorbance when 10 mM glutamate is added, but no metabolite 1 is added. An increase in absorbance indicates a higher amount of cell death. The striped bars show the amount of absorbance when varying amounts of metabolite 1 are added to the 10 mM glutamate treated cell culture. The extent that metabolite 1 inhibits cell death caused by glutamate is illustrated in the chart. Overall, the bar chart shows that as the amount of metabolite 1 increases, cell death is reduced.

We claim:

1. A method for treating age-related macular degeneration in a patient in need thereof, wherein said method comprises identifying a patient in need of treatment for age-related macular degeneration, and administering (S)—N-[2-[4-hydroxy-1,6,7,8-tetrahydro-2H-indeno[5,4-b]furan-8-yl]ethyl]propionamide to said patient.

2. The method of claim 1, wherein the patient is identified by visual examination of the patient.

3. The method of claim 1, wherein said age-related macular degeneration is the dry form.

4. The method of claim 1, wherein said age-related macular degeneration is the wet form.

5. The method of claim 1, wherein said age-related macular degeneration occurs in one eye.

6. The method of claim 1, wherein said age-related macular degeneration occurs in two eyes.

7. The method of claim 1, wherein said administration of (S)—N-[2-[4-hydroxy-1,6,7,8-tetrahydro-2H-indeno[5,4-b]furan-8-yl]ethyl]propionamide is by an oral dosage form.

8. The method of claim 1, wherein said administration of (S)—N-[2-[4-hydroxy-1,6,7,8-tetrahydro-2H-indeno[5,4-b]furan-8-yl]ethyl]propionamide is by an injectable dosage form.

9. The method of claim 1, wherein said administration of (S)—N-[2-[4-hydroxy-1,6,7,8-tetrahydro-2H-indeno[5,4-b]furan-8-yl]ethyl]propionamide is by a skin-patch dosage form.

10. The method of claim 1, wherein said administration of (S)—N-[2-[4-hydroxy-1,6,7,8-tetrahydro-2H-indeno[5,4-b]furan-8-yl]ethyl]propionamide is by a liquid, powder, ointment, paste, gel or cream dosage form.

11. The method of claim 1, wherein said (S)—N-[2-[4-hydroxy-1,6,7,8-tetrahydro-2H-indeno[5,4-b]furan-8-yl]ethyl]propionamide is administered in a dose of from 1 mg to 1000 mg.

12. The method of claim 1, wherein said (S)—N-[2-[4-hydroxy-1,6,7,8-tetrahydro-2H-indeno [5,4-b]furan-8-yl]ethyl]propionamide, is administered in a dose of from 1 mg to 1000 mg.

13. The method of claim 1, wherein said (S)—N-[2-[4-hydroxy-1,6,7,8-tetrahydro-2H-indeno[5,4-b]furan-8-yl]ethyl]propionamide is administered in a dose once daily.

14. The method of claim 13, wherein said (S)—N-[2-[4-hydroxy-1,6,7,8-tetrahydro-2H-indeno[5,4-b]furan-8-yl]ethyl]propionamide is administered in the evening.

15. The method of claim 13, wherein said (S)—N-[2-[4-hydroxy-1,6,7,8-tetrahydro-2H-indeno[5,4-b]furan-8-yl]ethyl]propionamide is administered prior to sleep.

16. The method of claim 1, wherein said (S)—N-[2-[4-hydroxy-1,6,7,8-tetrahydro-2H-indeno[5,4-b]furan-8-yl]ethyl]propionamide is administered in a dose twice daily.

17. The method of claim 1, wherein said (S)—N-[2-[4-hydroxy-1,6,7,8-tetrahydro-2H-indeno[5,4-b]furan-8-yl]ethyl]propionamide is administered in a dose more than twice daily.

18. The method of claim 1, further comprising administering photodynamic therapy.

19. The method of claim 1, further comprising administering therapeutic amount of a pharmaceutical agent selected from the group consisting of bevacizumab, ranibizumab, melatonin, pegatanib, and combinations thereof.

20. A method for treating age-related macular degeneration in a patient in need thereof, wherein said method comprises administering (S)—N-[2-[4-hydroxy-1,6,7,8-tetrahydro-2H-indeno[5,4-b]furan-8-yl]ethyl]propionamide to said patient.

21. The method of claim 20, wherein said (S)N-[2-[4 hydroxy-1,6,7,8-tetrahydro-2H-indeno[5,4-b]furan-8-yl]ethyl]propionamide administered in a dose of from 1 mg to 1000 mg.

22. The method of claim 20 further comprising administering photodynamic therapy.

23. The method of claim 20, further comprising administering therapeutic amount of a pharmaceutical agent selected from the group consisting of bevacizumab, ranibizumab, melatonin, pegatanib, and combinations thereof.

* * * * *